(12) United States Patent
Capote et al.

(10) Patent No.: US 11,058,437 B2
(45) Date of Patent: Jul. 13, 2021

(54) SYSTEMS AND METHODS FOR PEDICLE SCREW IMPLANTATION USING FLEXIBLE DRILL BIT

(71) Applicant: Zimmer Biomet Spine, Inc., Westminster, CO (US)

(72) Inventors: Allison Christine Capote, Boulder, CO (US); Adam Costanza, Aurora, CO (US); David Lee Skaggs, Los Angeles, CA (US); Frank J. Schwab, New York, NY (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 165 days.

(21) Appl. No.: 16/370,402

(22) Filed: Mar. 29, 2019

(65) Prior Publication Data

US 2019/0298392 A1    Oct. 3, 2019

Related U.S. Application Data

(60) Provisional application No. 62/650,198, filed on Mar. 29, 2018.

(51) Int. Cl.
| | |
|---|---|
| *A61B 17/16* | (2006.01) |
| *A61F 2/46* | (2006.01) |
| *A61B 17/17* | (2006.01) |
| *A61B 17/70* | (2006.01) |

(52) U.S. Cl.
CPC ...... *A61B 17/1631* (2013.01); *A61B 17/1615* (2013.01); *A61F 2/4611* (2013.01); *A61B 17/1757* (2013.01); *A61B 17/70* (2013.01)

(58) Field of Classification Search
CPC . A61B 17/1631; A61B 17/1615; A61B 17/70; A61B 17/1757; A61B 17/1671; A61F 2/4611
See application file for complete search history.

(56) References Cited

U.S. PATENT DOCUMENTS

| | | |
|---|---|---|
| 4,155,278 A | 5/1979 | Estok |
| 5,147,367 A | 9/1992 | Ellis |
| 5,403,322 A | 4/1995 | Herzenberg et al. |
| 5,474,558 A | 12/1995 | Neubardt |
| 5,601,550 A | 2/1997 | Esser |

(Continued)

OTHER PUBLICATIONS

Seehausen, Derek A, et al., "Safety and Efficacy of Power-Assisted Pedicle Tract Preparation and Screw Placement", Spine Deformity 3, (2015), 159-165.

(Continued)

*Primary Examiner* — Christian A Sevilla
(74) *Attorney, Agent, or Firm* — Schwegman Lundberg & Woessner, P.A.

(57) ABSTRACT

A method of implanting a bone anchor in a vertebra comprises engaging a tip of a flexible drill bit with boney structure of the vertebra, rotating the flexible drill bit at a slow speed, pushing the drill bit into exterior cortical bone of the boney structure of the vertebra, guiding the flexible drill bit into cancellous bone of the vertebra, receiving a tactile output generated by the flexible drill bit indicating resistance of interior cortical bone of the boney structure against the flexible drill bit, and reorienting a trajectory of the flexible drill bit toward the cancellous bone of the vertebra in reaction to the tactile output.

18 Claims, 11 Drawing Sheets

(56) References Cited

U.S. PATENT DOCUMENTS

| | | | |
|---|---|---|---|
| 5,728,128 A * | 3/1998 | Crickenberger | A61F 2/4657 606/102 |
| 5,851,207 A | 12/1998 | Cesarone | |
| 6,287,313 B1 | 9/2001 | Sasso | |
| 6,443,956 B1 * | 9/2002 | Ray | A61B 17/1671 606/80 |
| 6,514,258 B1 | 2/2003 | Brown et al. | |
| 6,562,046 B2 | 5/2003 | Sasso | |
| 6,849,047 B2 | 2/2005 | Goodwin | |
| 7,033,363 B2 | 4/2006 | Powell | |
| 7,131,974 B2 | 11/2006 | Keyer et al. | |
| 7,276,082 B2 | 10/2007 | Zdeblick et al. | |
| 7,357,804 B2 | 4/2008 | Binder, Jr. et al. | |
| 7,488,327 B2 | 2/2009 | Rathbun et al. | |
| 7,491,203 B2 | 2/2009 | Harris, Jr. et al. | |
| 7,623,902 B2 | 11/2009 | Pacheco | |
| 7,744,635 B2 | 6/2010 | Sweeney et al. | |
| 7,763,029 B2 | 7/2010 | Rathbun et al. | |
| 7,938,848 B2 | 5/2011 | Sweeney | |
| 7,942,668 B2 | 5/2011 | Brajnovic et al. | |
| 8,167,884 B2 | 5/2012 | Pacheco | |
| 8,214,014 B2 | 7/2012 | Pacheco | |
| 8,343,195 B2 | 1/2013 | Rathbun et al. | |
| 8,460,307 B2 | 6/2013 | Saidha et al. | |
| 8,465,491 B2 | 6/2013 | Yedlicka et al. | |
| 8,469,963 B2 | 6/2013 | Shoham | |
| 8,617,209 B2 | 12/2013 | Sweeney et al. | |
| 8,808,338 B2 | 8/2014 | Martin | |
| 8,882,773 B2 | 11/2014 | Bourque et al. | |
| 8,932,303 B2 | 1/2015 | Bouliane | |
| 8,951,264 B2 | 2/2015 | Saidha et al. | |
| 8,974,466 B2 | 3/2015 | Powell | |
| 8,986,354 B2 | 3/2015 | Walker | |
| 9,168,151 B2 | 10/2015 | Sweeney et al. | |
| 9,232,954 B2 | 1/2016 | Steiner et al. | |
| 9,326,779 B2 | 5/2016 | Dorawa et al. | |
| 9,468,477 B2 | 10/2016 | Martin | |
| 9,480,488 B2 | 11/2016 | Powell | |
| 9,498,229 B2 | 11/2016 | Harris, Jr. et al. | |
| 9,549,744 B2 | 1/2017 | Pommer et al. | |
| 9,554,834 B2 | 1/2017 | Saidha et al. | |
| 9,662,125 B2 | 5/2017 | Bourque et al. | |
| 2004/0064058 A1 * | 4/2004 | McKay | A61F 2/4601 600/506 |
| 2006/0149245 A1 | 7/2006 | Sweeney | |
| 2006/0264956 A1 * | 11/2006 | Orbay | A61B 17/1615 606/80 |
| 2007/0055239 A1 | 3/2007 | Sweeney et al. | |
| 2007/0161427 A1 | 7/2007 | White | |
| 2008/0200918 A1 | 8/2008 | Spitler et al. | |
| 2009/0012526 A1 | 1/2009 | Fletcher | |
| 2010/0311028 A1 * | 12/2010 | Bell, III | G09B 23/28 434/263 |
| 2011/0213426 A1 | 9/2011 | Yedlicka et al. | |
| 2012/0203288 A1 | 8/2012 | Lange et al. | |
| 2012/0253353 A1 | 10/2012 | McBride | |
| 2013/0023881 A1 | 1/2013 | Cook et al. | |
| 2013/0131684 A1 | 5/2013 | Farrell | |
| 2013/0261628 A1 | 10/2013 | Burley et al. | |
| 2013/0296864 A1 | 11/2013 | Burley et al. | |
| 2014/0005670 A1 | 1/2014 | Fletcher | |
| 2014/0316414 A1 | 10/2014 | Steiner et al. | |
| 2015/0127012 A1 | 5/2015 | Pilgeram et al. | |
| 2016/0183995 A1 * | 6/2016 | Zrinski | A61B 17/88 606/96 |
| 2016/0324552 A1 | 11/2016 | Baker et al. | |
| 2017/0021480 A1 | 1/2017 | Hohmann et al. | |
| 2017/0105771 A1 | 4/2017 | Saidha et al. | |
| 2017/0181774 A1 | 6/2017 | Cahill | |
| 2017/0209154 A1 | 7/2017 | Krause et al. | |
| 2017/0209158 A1 | 7/2017 | Williams | |
| 2017/0296245 A1 | 10/2017 | Gault et al. | |
| 2017/0333056 A1 | 11/2017 | Ponzer et al. | |

OTHER PUBLICATIONS

Skaggs, David L, et al., "Master Techniques in Orthopaedic Surgery", Pediatrics, Second Edition; Pedicle Screw Insertion—Manual Power Techniques, (2015), pp. 573-575.

* cited by examiner

SYSTEMS AND METHODS FOR PEDICLE SCREW IMPLANTATION USING FLEXIBLE DRILL BIT

CLAIM OF PRIORITY

This application claims the benefit of U.S. Provisional Patent Application Ser. No. 62/650,198, filed on Mar. 29, 2018, the benefit of priority of which is claimed hereby, and which is incorporated by reference herein in its entirety.

TECHNICAL FIELD

This document pertains generally, but not by way of limitation, to systems and methods for bone anchor implantation. More specifically, but not by way of limitation, the present application relates to pedicle screw implantation using powered drill bits.

BACKGROUND

A spinal column can require correction of spinal deformities and abnormalities resulting from trauma or degenerative issues. Various methods of correcting issues with the spinal column can include fusing adjacent vertebrae together or immobilizing the spinal column with a rod system. For example, fasteners or other fixation devices can be attached to each vertebra, with each fastener serving as an anchor point for attaching the rod. Rods can be placed on either side of the spinal column to span several vertebrae. The fasteners are carefully inserted into the vertebrae at a pedicle area of the bone. Ideally, the trajectory of the fastener is controlled to ensure the fastener passes straight through the pedicle into the vertebral body without intersecting the vertebral foramen where the spinal cord is located. However, inexperience or unusual bone conditions can infrequently lead to undesirable penetration or near penetration of the vertebral foramen, which can sometimes result in harm to the patient. A surgeon typically relies on personal understanding of spinal anatomy and skill to place each fastener. Typically, each fastener is inserted manually after first tapping the pedicle with a manual pilot drill. Some spinal correction procedures can involve placement of many fasteners, which can result in surgeon fatigue.

Examples of methods for pedicle screw implantation are described in U.S. Pat. No. 6,849,047 to Goodwin; U.S. Pat. No. 9,549,744 to Pommer et al.; and U.S. Pub. No. 2017/0181774 to Cahill. U.S. Pub. No. 2013/0296864 to Burley et al. describes a flexible drill bit for use in minimally invasive orthopedic procedures.

OVERVIEW

The present inventors have recognized, among other things, that a problem to be solved can include the inability of surgeons to readily feel placement of a drill bit when implanting a pedicle screw, particularly in powered drill applications. Specifically, the present inventors have recognized that the use of powered drilling in the spinal column has been avoided by surgeons due to loss of tactile feedback compared to manual drilling procedures. For example, the aforementioned publication to Cahill teaches away from the complete use of powered drilling when implanting pedicle screws due to loss of tactile feel. As such, fatigue associated with repeated manual drilling operations can result in inaccurate pedicle screw placement as well as a reducing in the number of surgeries that can be safely performed in a particular time period.

The present subject matter can help provide a solution to this problem, such as by providing tactile feedback of a powered drill bit used for pedicle screw implantation. In particular, powered drilling of vertebral pilot channels can be performed using a flexible drill bit the transmits tactile sensation to the surgeon, thereby permitting the surgeon to feel differences in cortical and cancellous bone through the drill bit even when being rotated by an external power source. The flexible drill bit can be rotated at slow speeds, e.g., one to three revolutions per second, to facilitate transmission of tactile feel from the bone to the hand of the surgeon. The flexible drill bit can be rotated slow enough so that the force of the impact of a cutting head of the flexible drill bit on cortical bone is not overwhelmed and muted out by the speed of the cutting head cutting through the cortical bone. Additionally, the diameter of the shaft of the flexible drill bit can be sized to permit the cutting head to deflect upon impact with cortical bone and transmit a vibration associated with the impact through the drill bit.

In an example, a method of implanting a bone anchor in a vertebra comprises engaging a tip of a flexible drill bit with boney structure of the vertebra, rotating the flexible drill bit at a slow speed, pushing the drill bit into exterior cortical bone of the boney structure of the vertebra, guiding the flexible drill bit into cancellous bone of the vertebra, receiving a tactile output generated by the flexible drill bit indicating resistance of interior cortical bone of the boney structure against the flexible drill bit, and reorienting a trajectory of the flexible drill bit toward the cancellous bone of the vertebra in reaction to the tactile output.

In another example, a method of implanting a pedicle screw into a pedicle of a vertebra comprises determining a trajectory for a pedicle screw shaft into a cancellous bone canal behind a cortical bone wall to avoid interior cortical bone, engaging a tip of a drill bit having a tapered shaft with a starting point of the trajectory on the cortical bone wall of the pedicle of the vertebra, rotating the drill bit using rotational input from a powered driver, pushing the powered driver to penetrate the tip of the drill bit through the cortical bone wall along the trajectory, guiding the drill bit into the cancellous bone canal, sensing engagement of the tip of the drill bit with the interior cortical bone, and reorienting the drill bit along the trajectory away from the interior cortical bone.

In yet another example, a sliding sleeve can be used in conjunction with powered shafts of the present disclosure. For example, a sliding sleeve can be used with a powered pedicle screw driver shaft to provide a location for a surgeon to grasp, and thereby guide and steady, the driver shaft. In another example, a sliding sleeve can be used with a powered flexible drill bit to provide a location for receiving tactile feedback from the flexible drill bit, in addition to providing a location for a surgeon to grasp, and thereby guide and steady, the flexible drill bit.

This overview is intended to provide an overview of subject matter of the present patent application. It is not intended to provide an exclusive or exhaustive explanation of the invention. The detailed description is included to provide further information about the present patent application.

Figure 1:
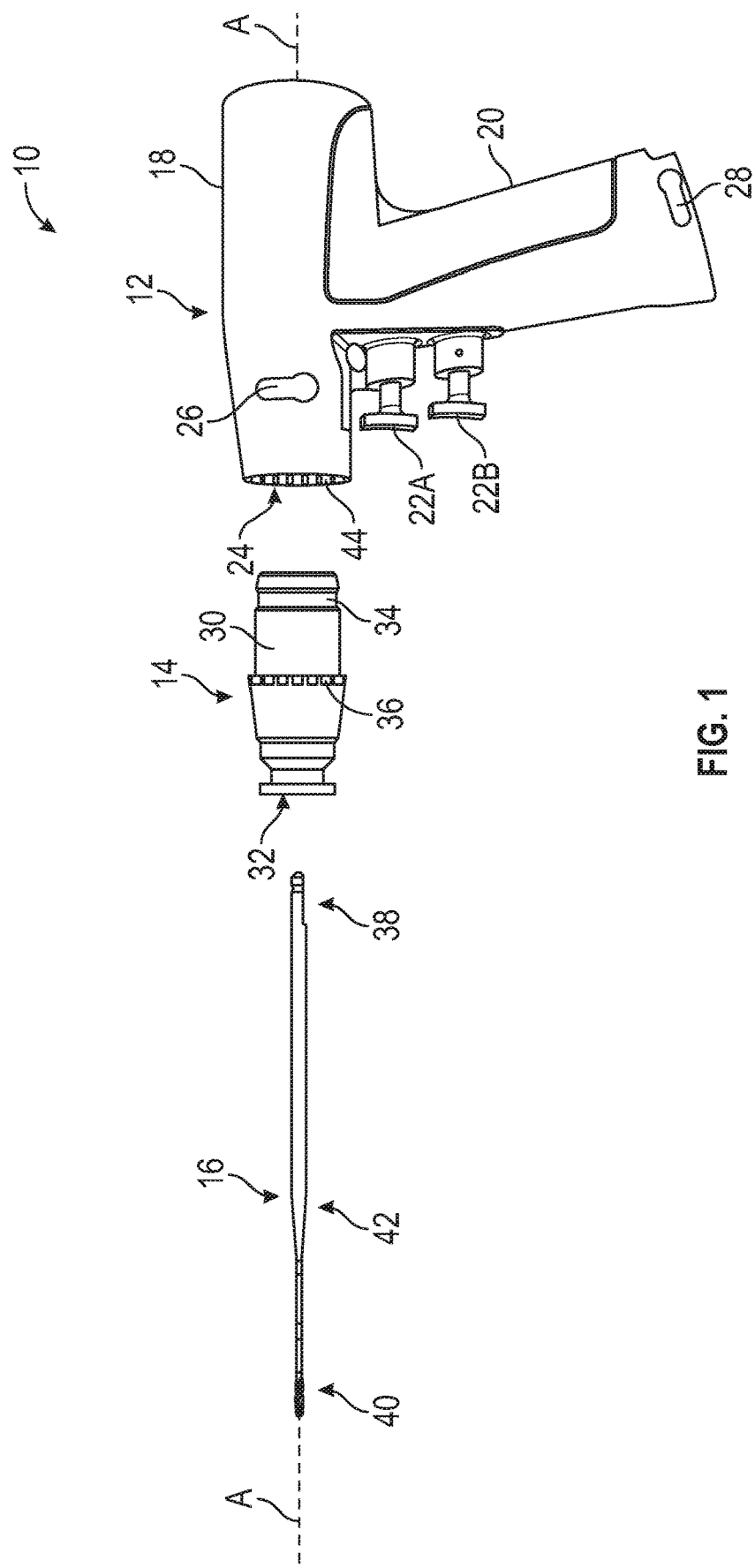
FIG. 1 is an exploded view of a powered drill bit system comprising a powered driver, a gear system and a drill bit.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1 is an exploded view of powered drill bit system 10 comprising powered driver 12, gear system 14 and drill bit 16. Powered driver 12 can comprise motor housing 18, handle 20, first control trigger 22A, second control trigger 22B, gear system socket 24, gear system lock 26 and battery lock 28. Gear system 14 can comprise housing 30 in which can be disposed a gear system (not shown). Housing 30 can also comprise drill bit socket 32 as well as features for engaging socket 24, such as channel 34 and teeth 36.

Housing 30 can also include features (not shown) at socket 32 for engaging and retaining drill bit 16. Drill bit 16 can comprise proximal end 38 that can include features for engaging socket 32, distal end 40 that can include features for removing bone, and intermediate portion 42 that can include a flexible shaft that is adapted for performing implantation of bone anchors such as pedicle screw shafts.

Powered drill bit system 10 can be used to perform pedicle screw implantation procedures as described herein, as well as other procedures. Powered driver 12 can be used to generate rotational output for rotating drill bit 16, among other attachments. For example, one or both of control triggers 22A and 22B can be actuated to cause a motor (not shown) within motor housing 18 to rotate. Control trigger 22A can be configured to generate low speed rotation at socket 32 in a first direction and trigger 22B can be configured to cause high speed rotation at socket 32 in the first direction, such as by controlling the amounts of electrical powered delivered from a battery (now shown) within handle 20 to the motor. Additionally, control triggers 22A and 22B can be simultaneously depressed to cause rotation of socket 32 in the opposite direction as the first direction. Additionally, control triggers 22A and 22B can variably control the speed of the motor based on their displacement. For example, further depressing control triggers 22A and 22B toward handle 20 can cause faster rotational output of the motor.

Gear system lock 26 can comprise a button or lever that can engage channel 34 of housing 30 to prevent displacement of gear system 14 along rotational axis A. Teeth 36 of housing 30 can engage mating teeth 44 in socket 24 to prevent rotation of housing 30 about rotational axis A. Socket 32 can rotate within housing 30 via engagement with the motor in housing 18. Gear system lock 26 can be depressed to permit gear system 14 to be removed from socket 24. Gear system 14 can be used to reduce, or otherwise change, the output speed of powered drill bit system 10. For example, gear system 14 can include a gear train that receives input from the motor in housing 18 and reduces that speed to an output speed that is input into socket 32, thus causing drill bit 16 to rotate at a speed slower than the motor. Using gear system 14 as a gear reduction system provides a surgeon with additional control over the slow speed operation of the drill bit or other instrument attached to the powered drill bit system 10. For example, in one configuration, gear system 14 can be configured to limit rotational output of flexible drill bit 16 to a safe speed for pilot hole drilling in a pedicle, and flexible drill bit 16 can include can include proximal end 38 that can be configured to only mate with gear system 14.

As is discussed in greater detail with reference to FIG. 2, proximal end 38 can include features for engaging socket 32 to maintain connection of drill bit 16 to gear system 14, and distal end 40 can include features for removing bone. Intermediate portion 42 can comprise a flexible portion that is configured to transmit rotational shaft power from proximal end 38 to distal end 40, while permitting proximal end 38 to be displaced off-axis from proximal end 38 while rotating. Flexing of intermediate portion 42 can be detected by a user of powered drill bit system 10. As such, the user of powered drill bit system 10 can receive tactile feedback when drill bit 16 flexes, such as when drill bit 16 transitions from engaging a first substance with a first density to engaging a second substance with a second, lower density, such as cortical and cancellous bone. In a specific example, the off-axis displacement characteristics are configured to permit distal end 40 to cut cortical and cancellous bone when sufficient axil force is applied to drill bit 16 by a user, while also allowing distal end 40 to be displaced off-axis when distal end 40 engages cortical bone from the side. As discussed below with reference to FIGS. 6-9, sliding sleeve 78 can be used with system 10. In various embodiments, sliding sleeve 78 can be used to receive or enhance the perception of the tactile feedback generated by flexible drill bit 16, in addition to providing a location for the surgeon to grasp flexible drill bit 16 to guide and steady flexible drill bit 16.

Figure 2:
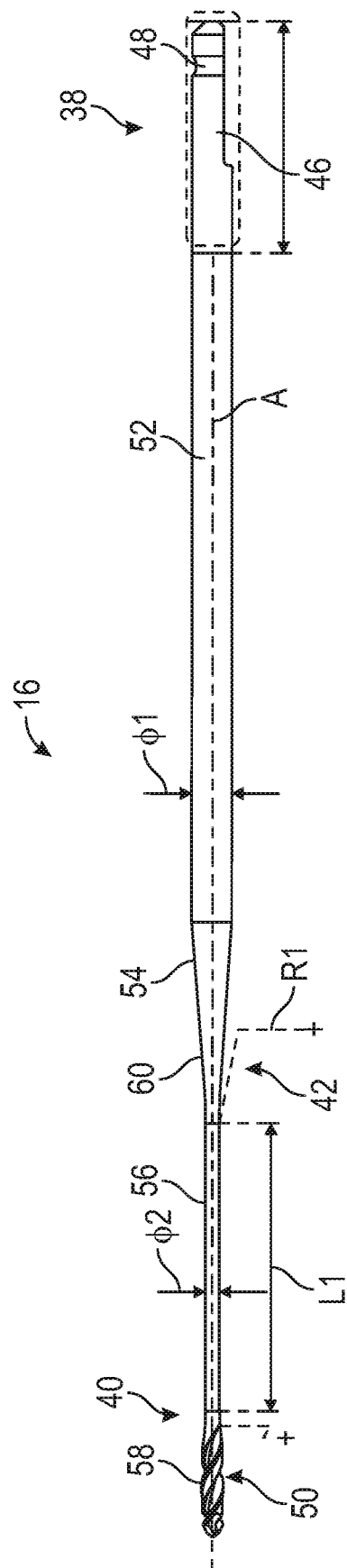
FIG. 2 is a side view of an embodiment of the drill bit of FIG. 1 comprising a flexible drill bit comprising a cutting head, a flexible shaft and a coupling portion.
Figure 3A:
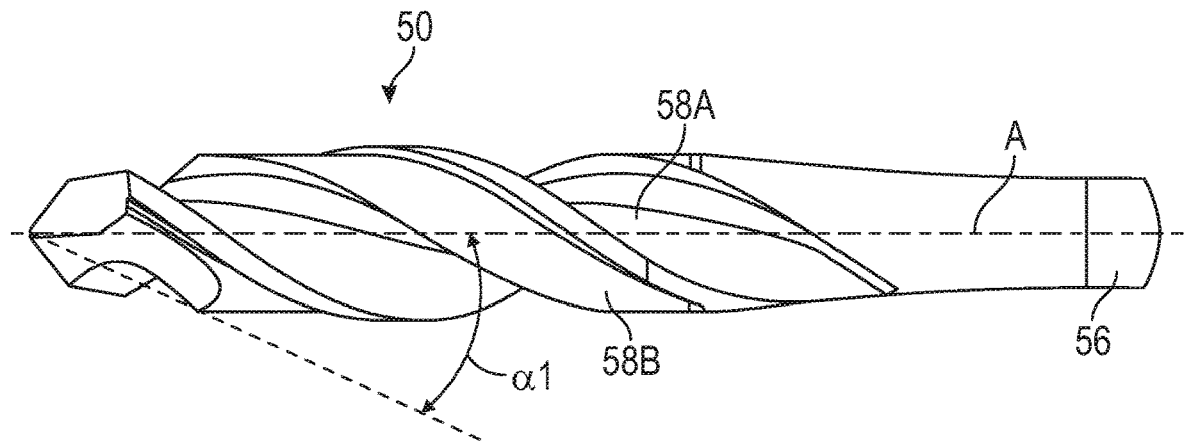
FIG. 3A is a first close-up side view of the cutting head of the flexible drill bit of FIG. 2 showing a gash angle for cutting surfaces for use in cutting bone.
Figure 3B:
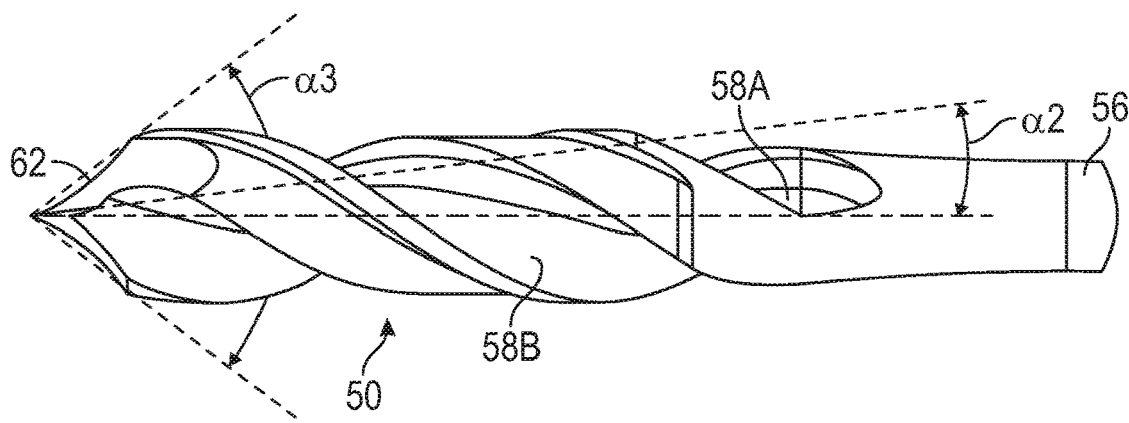
FIG. 3B is a second close-up side view of the cutting head of the flexible drill bit of FIG. 2 showing a rake angle for cutting surfaces for use in cutting bone.
Figure 4:
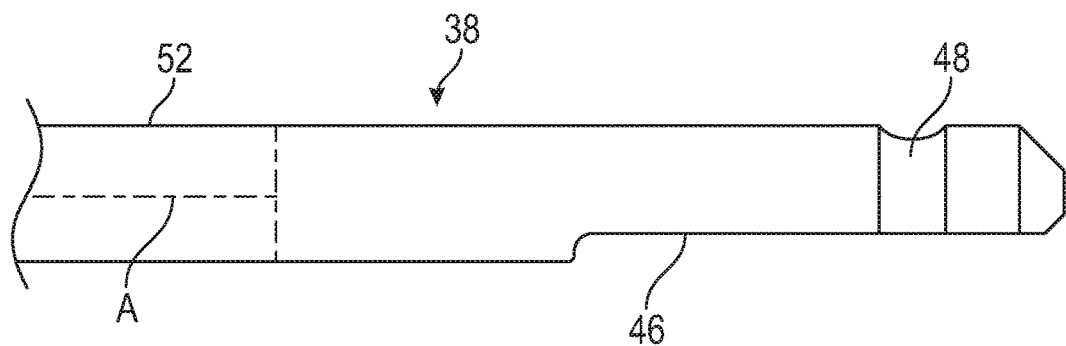
FIG. 4 is a close-up view of the coupling portion of the flexible drill bit of FIG. 2 showing torque transfer and retaining features.

FIG. 2 is a side view of an embodiment of drill bit 16 of FIG. 1 comprising proximal end 38, distal end 40 and intermediate portion 42. Proximal end 38 can comprise flat 46 and channel 48. Distal end 40 can comprise cutting head 50. Intermediate portion 42 can comprise first drive shaft 52, neck 54 and second drive shaft 56. FIG. 3A is a first close-up side view of cutting head 50 of flexible drill bit 16 of FIG. 2 showing gash angle α1 for cutting surfaces for use in cutting bone. FIG. 3B is a second close-up side view of cutting head 50 of flexible drill bit 16 of FIG. 2 showing rake angle α2 for cutting surfaces for use in cutting bone. FIG. 4 is a close-up view of proximal end 38 of flexible drill bit 16 of FIG. 2 showing flat 46 and channel 48. FIGS. 2-4 are discussed concurrently.

Flat 46 and channel 48 can be used to retain drill bit 16 within socket 24 (FIG. 1). For example, flat 46 can engage a rotating drive member of gear system 14, which is coupled to powered driver 12 and can be configured to receive torque from the rotating drive member and transmit the torque to first drive shaft 52. Channel 48 can engage with a retaining member of powered driver 12 and can be configured to resist axial displacement of drill bit 16 along rotational axis A. For example, ball bearings within socket 24 can be pushed into channel 48 to inhibit axial displacement while permitting rotation along rotational axis A.

First drive shaft 52 can extend from proximal end 38 along rotational axis A. Drive shaft 52 can comprise an elongate body configured to transmit torque from proximal end 38 to neck 54. In an example, drive shaft 52 can comprise a cylindrical body, but can have other configurations such as hexagonal. Neck 54 can comprise a transition body between first drive shaft 52 and second drive shaft 56. Neck 54 can be configured to reduce stress that might otherwise result in an abrupt transition between the different sizes of first drive shaft 52 and second drive shaft 56. Neck 54 can have a conical shape, but can comprise other configurations such as curved or sloped surfaces that smoothly blend together. As discussed below, neck 54 can also include a curved surface to transition into second drive shaft 56 with producing an edge or stress concentration. Second drive shaft 56 can extend from neck 54 along rotational axis A. Drive shaft 56 can comprise an elongate body configured to transmit torque from proximal neck 54 to cutting head 50. In an example, drive shaft 56 can comprise a cylindrical body, but can have other configurations such as hexagonal. Cutting head 50 can include one or more cutting flutes, such as flutes 58A and 58B, that are shaped to form edges configured to cut bone. Cutting head 50 can be bulbous compared to the diameter of drive shaft 56 or can have the same diameter as drive shaft 56.

Drill bit 16 is sized and shaped, and made from a desired material, to perform with desired mechanical properties to transmit torque to cutting head 50 from proximal end 38, while also permitting flexure of second drive shaft 56 and transmission of vibration from cutting head 50 to proximal end 38. In examples, drill bit 16 can be fabricated from a rigid material that transmits torque and is resistant to bending while permitting some bending, depending on the thickness of the shaft. In example, drill bit can be fabricated from stainless steel. In an example, drill bit 16 is fabricated from 465 Stainless Steel per ASTM F899.

As shown in FIGS. 3A and 3B, cutting head 50 can include cutting edge 62 that forms the axial rake angle α2. Cutting edge 62 can be disposed at gash angle α1. Additionally, flutes 58A and 58B can form point angle α3. First drive shaft 52 can have a first diameter of Ø1 and second drive shaft 56 can have a second diameter of Ø2. First diameter Ø1 can be larger than second diameter Ø2 to, for example, help ensure that bending will occur along second drive shaft 56 before or in place of any bending of first drive shaft 52. In an example, first drive shaft 52 can have a first diameter Ø1 of approximately 4.47 mm and second drive shaft 56 can have a second diameter Ø2 of approximately 1.5 mm. The present inventors have found that a second diameter Ø2 of 1.5 mm is well suited for bending and transmitting vibration without sacrificing too much strength. In examples, second diameter Ø2 can be in a range of +/−0.5 mm of 1.5 mm. Second drive shaft 56 can be in a range of +/−0.5 mm of 4.47 mm. However, other diameters for first diameter Ø1 and second diameter Ø2 can be used to generate desirable bending of second drive shaft 56 as described herein. In examples, flexible drill bit can have three different sections, each with varying lengths designed to maximize strength, flexibility and vibration transmission, a drill tip section, a flexible section and a stiffer shaft section for coupling to driver. In an example, second drive shaft 56 can have a length L1 of approximately 32.6 mm, however other lengths can be used to generate desirable bending of second drive shaft 52 as described herein. First drive shaft 56 and second drive shaft 56 can be connected at a necked-down, tapered or smooth transition region or section. In an example, neck 54 can include a curved surface 60 that can have a radius RI of approximately 40 mm. Curved surface 60 can be tangent to the outer surface of second drive shaft 56. Cutting head 50 can be provided with tip 68 having gash angles α1 and α2 that provides desirable cutting features, such as are conducive to reaming bone in a smooth matter without generating vibration that interferes with vibrations being transmitted through second drive shaft 56. In an example, gash angle α1 can be approximately 24°+/−2°. In an example, rake angle α2 can be approximately 7°+/−2°. In an example, point angle α3 can be approximately 81.8°. The present inventors have found that the foregoing combination of features provides sufficient flexibility in second drive shaft 56 to transmit the feel of cutting edge 62 engaging bone through first drive shaft 52 to a user of powered driver 12 at handle 20 (FIG. 1).

Figure 5:
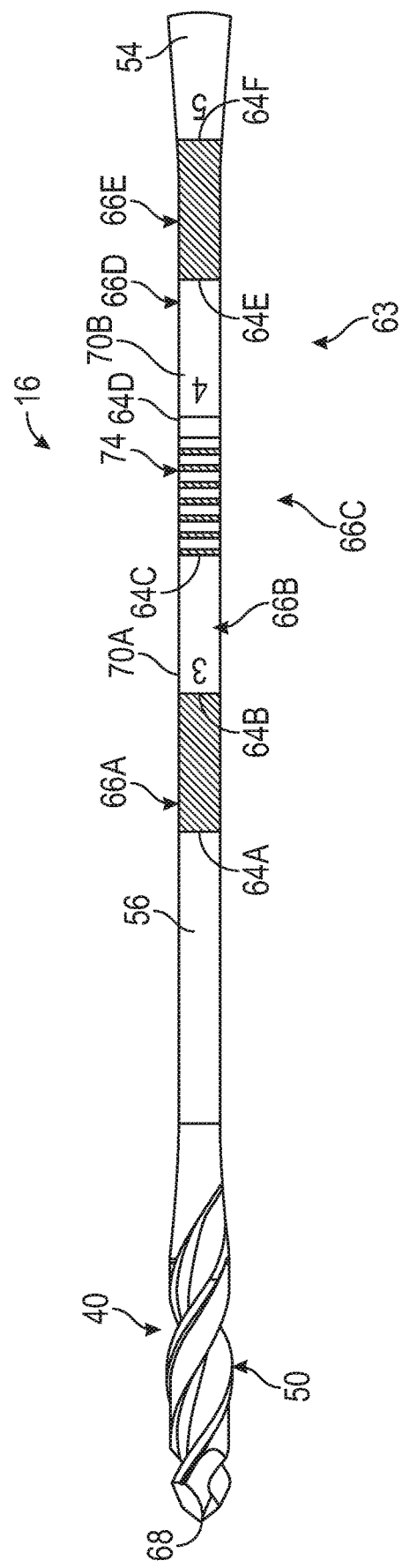
FIG. 5 is a close-up side view of the cutting head and flexible shaft of FIG. 2 showing graduation marks and bands that can be used for depth control.

FIG. 5 is a close-up side view of cutting head 50 and flexible shaft 56 of FIG. 2 showing indicators 63 comprising graduation marks 64A-64F and graduation bands 66A-66E that can be used for depth control. Graduation marks 64A-64F can be used to indicate the length of flexible drill bit 16 from tip 68 to the specific graduation mark. Indicia 70A and 70B can be included on drive shaft 56 to indicate the magnitude of each graduation mark, such as with Arabic numerals. For example, each of graduation marks 64A-64F indicate a depth of a half a centimeter, with graduation mark 64A indicating a depth of 2.5 cm and graduation mark 64F indicating a depth of 5.0 cm. Thus, each band can encompass a corresponding 0.5 cm. Each of bands 64A-64F can further include additional half marks to indicate smaller depth increments, such as millimeters. For example, band 64C can include hash marks 74. The various graduation bands, graduation marks and hash marks can correspond to the lengths of fastener shafts of bone anchors commonly used in pedicle screw implantation procedures.

Figure 6:
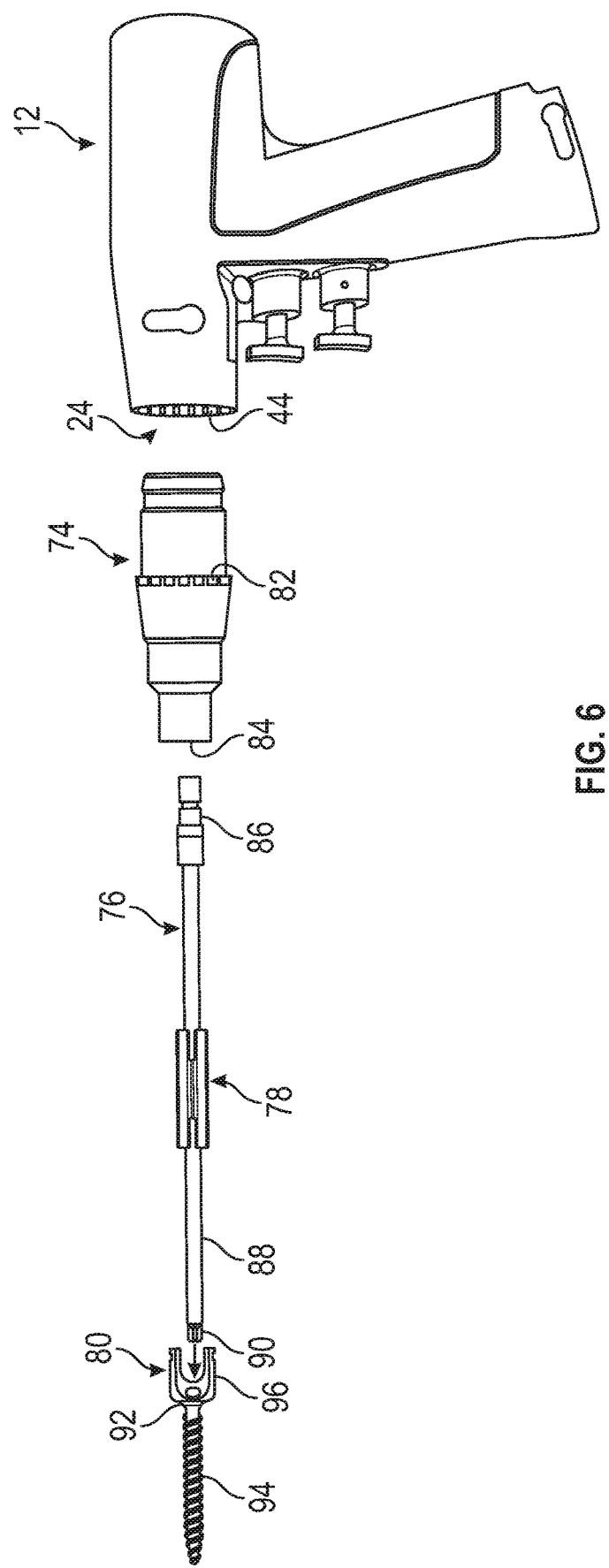
FIG. 6 is an exploded view of the powered driver of FIG. 1 shown with a gear system, a pedicle screw driver shaft, a sliding sleeve device and a pedicel screw.

FIG. 6 is an exploded view of powered driver 12 of FIG. 1 shown with gear system 74, pedicle screw driver shaft 76, sliding sleeve 78 and pedicle screw 80. Powered driver 12 can function as described previously. Gear system 74 can comprise teeth 82 and socket 84. Driver shaft 76 can comprise coupler 86, shaft 88 and tip 90. Pedicle screw 80 can comprise head 92, threaded shaft 94 and housing 96.

Teeth 44 of gear system socket 24 can be configured to mate with teeth 82 of gear system 74. Gear system 74 can operate in a similar manner as gear system 14, but can include a different socket than drill bit socket 32. For example, gear system 74 can include driver socket 84, which can be configured to mate with coupler 86 of driver shaft 76. Coupler 86 can include features to transmit torque from gear system 74 to shaft 88 of driver shaft 76 and to prevent driver shaft 76 from being axially separated from gear system 74. Gear system 74 can additionally include gearing that is different than gear system 14 to provide different rotational output speeds for driver shaft 76 that can be more conducive for driving pedicle screw 80 as compared to rotational output speeds that are more conducive for tapping and drilling operations. Driver shaft 76 can also include driver tip 90 that can be configured to mate with a corresponding socket (not visible in FIG. 6) in head 92 of pedicle screw 80. In an example, tip 90 can comprise a hexalobe driver. Pedicle screw 80 can also include threaded shaft 94 that can extend from head 92 to engage with boney structure of a pedicle of a vertebra. Housing 96 can be coupled to head 92 to receive a rod or other support structure that is to be attached to the vertebra via pedicle screw 80. Sleeve 78 can be configured to slide onto driver shaft 76 by slipping over tip 90. Sleeve 78 can be used as a handle for a surgeon or other operator of system 10 to grasp driver shaft 76 while implanting pedicle screw 80 to guide or steady driver shaft 76.

In embodiments, sleeve 78 can be configured to mount and slide onto flexible drill bit 16, such as at drive shaft 52. As discussed herein, sleeve 78 can be used to guide and steady flexible drill bit 16. Additionally, sleeve 78 can be configured to assist in sensing vibration from flexible drill bit 16 to, for example, eliminate having to sense vibration through powered driver 12 at handle 20.

Figure 7:
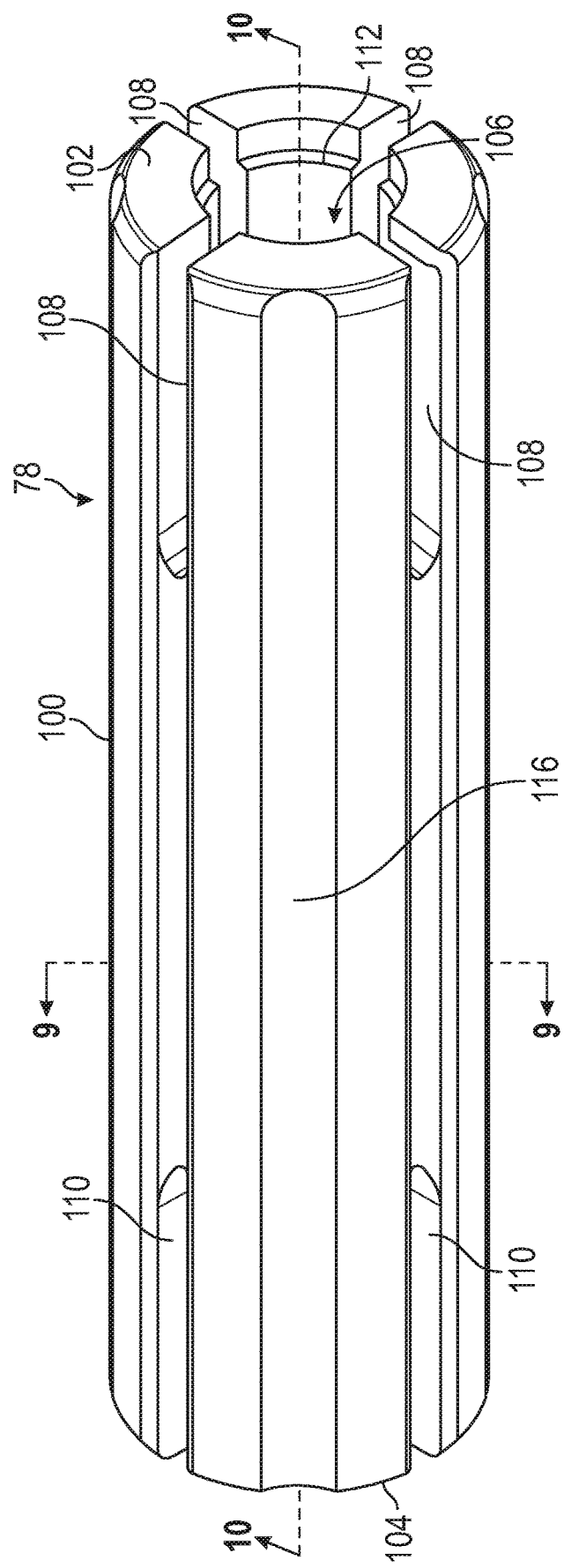
FIG. 7 is a perspective view of the sliding sleeve device of FIG. 6.
Figure 8:
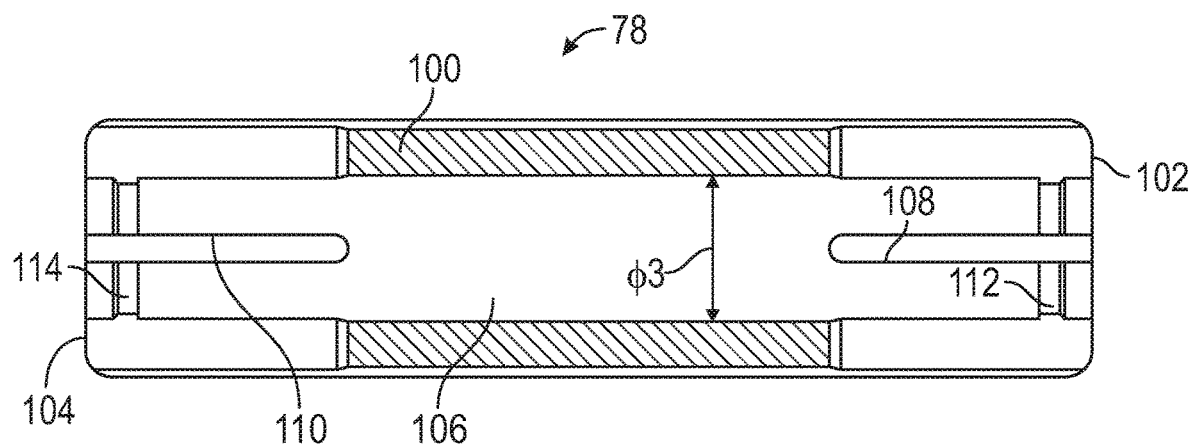
FIG. 8 is a side cross sectional view of the sliding sleeve device of FIG. 7 taken at section 8-8.
Figure 9:
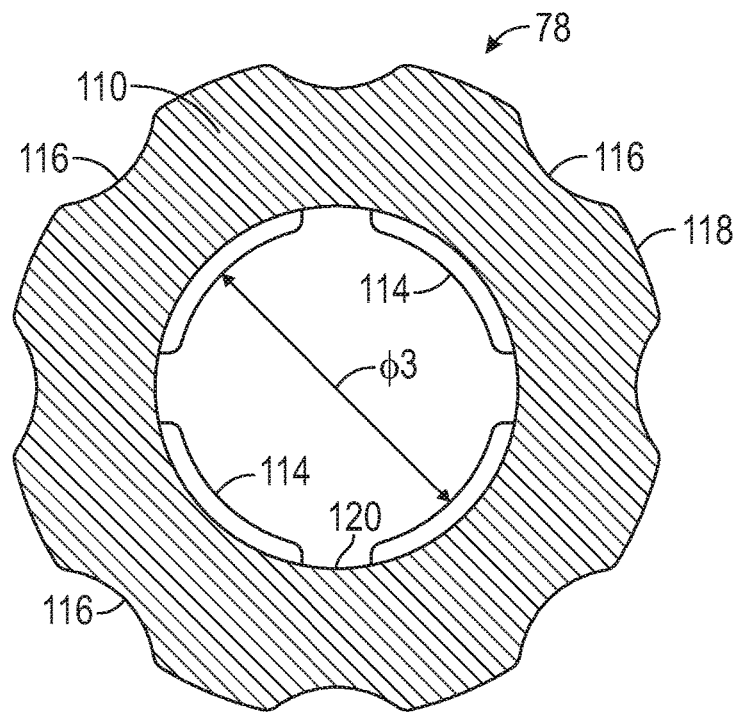
FIG. 9 is an end cross-sectional view of the sliding sleeve device of FIG. 7 take at section 9-9.

FIG. 7 is a perspective view of sleeve 78 of FIG. 6. Sleeve 78 can comprise main body 100, first end 102, second end 104, through-bore 106, first cut-outs 108, second cut-outs 110, first rib 112, second rib 114 (FIG. 9) and flutes 116. FIG. 8 is a side cross sectional view of sleeve 78 of FIG. 7 taken at section 8-8. FIG. 9 is an end cross-sectional view of sleeve 78 of FIG. 7 take at section 9-9. FIGS. 7-9 are discussed concurrently.

Sleeve 78 can be made of a single piece of material defined by main body 100. In an example, sleeve 78 can be fabricated from a polymer material. In examples, the material is non-abrasive and resilient. Main body 100 can be generally cylindrical in shape. As can be seen in FIG. 9, outer surface 118 of main body 100 can be circular, but for flutes 116. Flutes 116 can form edges along part of the length of main body 100 that provide grip-enhancements. First cut-outs 108 and second cut-outs 110 can extend into main body from ends 102 and 104, respectively, to provide sleeve 78 with a degree of flexibility or springiness toward ends 102 and 104. Through-bore 106 can extend all the way through main body 100 from first end 102 to second end 104. Through-bore 106 can have a diameter Ø3 that can be approximately the same diameter as driver shaft 76, or slightly larger. Ribs 112 and 114 can extend from inner surface 120 of through-bore 106. Main body 100 can flex outward along cut-outs 108 and cut-outs 110. With main body 100 not flexed, the diameter of through-bore 106 at ribs 112 and 114 can be smaller than the diameter of driver shaft 76. When sleeve 78 is positioned onto driver shaft 76, driver shaft 76 will push against ribs 112 and 114, causing main body to flex at cut-outs 108 and 110. Thus, ribs 112 and 114 will be pushed into engagement with driver shaft 76 to support sleeve 78. With diameter Ø3 being slightly larger than the diameter of driver shaft 76, inner surface 120 will be spaced from driver shaft 76 so that sleeve 78 is mostly floating relative to driver shaft 76, but for the presence of ribs 112 and 114.

Main body 100 is configured to freely slide along the length of driver shaft 76 (FIG. 6). Ribs 112 and 114 can be used to space main body 100 from the outer surface of driver shaft 76 to reduce friction therebetween so that sleeve 78 more readily floats relative to driver shaft 76. As such, ribs 112 and 114 provide a friction fit or interference fit with driver shaft 76 to permit sleeve 78 to support the weight of sleeve 78. As such, without being acted upon, sleeve 78 will remain in position along driver shaft 76 unless acted upon by a surgeon or operator of system 10. Thus, a surgeon can slide sleeve 78 axially along the length of driver shaft 76. Additionally, a surgeon can grip sleeve 78 while applying rotational power to driver shaft 76 from powered driver 12 (FIG. 6) and driver shaft 76 can rotate within sleeve 78 while sleeve 78 is gripped. As such, a surgeon can hold onto sleeve 78 to steady drive shaft 76 and more accurately guide pedicle screw 80 into the target site on the bone. Flutes 116 can inhibit sleeve 78 from slipping within the hand of the surgeon. In additional embodiments, ribs 112 and 114 can be used to couple with features of driver shaft 76 to axially lock sleeve 78 in place. For example, ribs 112 and 114 can slip into grooves provided along driver shaft 76 to position sleeve 78 in a desired location along driver shaft 76, such as near coupler 86, to position sleeve 78 out of the way, or near tip 90, to position sleeve 78 in an advantageous position for pedicle screw guidance.

Figure 10:
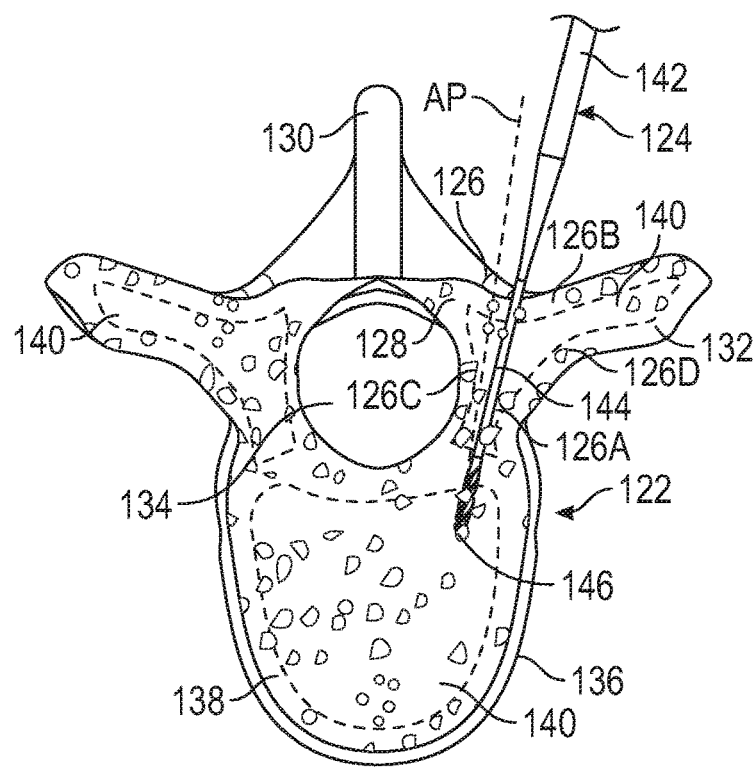
FIG. 10 is a diagrammatic superior view of a cross-section of a vertebra showing a probe inserted into a pedicle for preparation of a pilot drill bit.

FIG. 10 is a diagrammatic superior view of a cross-section of vertebra 122 showing probe 124 inserted into pedicle 126 for preparation of a pilot drill bit. Vertebra 122 includes pedicle 126, lamina 128, spinous process 130, transverse process 132, vertebral foramen 134 and body 136. Vertebra 122 is comprised of outer cortical bone 138 and inner cancellous bone 140. As is understood in the art, cancellous bone 140 is softer and less dense than cortical bone. Pedicle 126 at least partially defines a narrow passage of bone between vertebral foramen 134 and the exterior of vertebra 122. Pedicel 126 thus includes an even narrower passage of cancellous bone 140 therein, identified in FIG. 10 as cancellous bone canal 126A. Cancellous bone canal 126A can be bound by outer cortical wall 126B and interior cortical walls 126C and 126D. As is known in the art, nerve tissue including the spinal cord is located within vertebral foramen 134. As such, it is desirable to avoid penetrating into vertebral foramen 134 with pedicle screw 80. Thus, it is desirable to insert pedicle screw 80 into pedicle 126 straight along a trajectory coincident with axis $A_P$.

Probe 124 can comprise handle portion 142 and probe portion 144, which terminates at tip 146. Probe portion 144 can be curved as shown in FIG. 10 such that tip 146 can extend along axis $A_P$, while handle portion 142 is angled relative to axis $A_P$. Probe 124 is configured for manual operation by a surgeon or operator of system 10. As such, handle portion 142 can comprise an elongate shaft for manipulation by the hand of the surgeon. Conventionally, a surgeon would use probe 124 to prepare an entry site for a reamer, tap and pedicel screw. However, with curved probes, such as probe 124, surgeons have a tendency to medialize the trajectory of the probe due to the curve. Medializing the probe can potentially incur the risk of medial breach of vertebral foramen 134. With the use of flexible drill bit 16, a pilot hole can be drilled, as discussed with reference to FIG. 11, without having to medialize drill bit 16. As such probe 124 need not be used to form a pilot hole in vertebra 122. However, probe 124, or an awl, power bur, curette, or a different straight probe can be used to make anatomic marking on vertebra 122. For example, probe 124 can be used to make a small centering hole or dimple in pedicle 126 in which flexible drill bit 16 can be positioned to prevent flexible drill bit 16 from running off of vertebra 122 when power is applied to drill bit 16. In an example, the centering hole can penetrate through the outer cortical bone 138 to provide an unobstructed path to cancellous bone 140.

Figure 11:
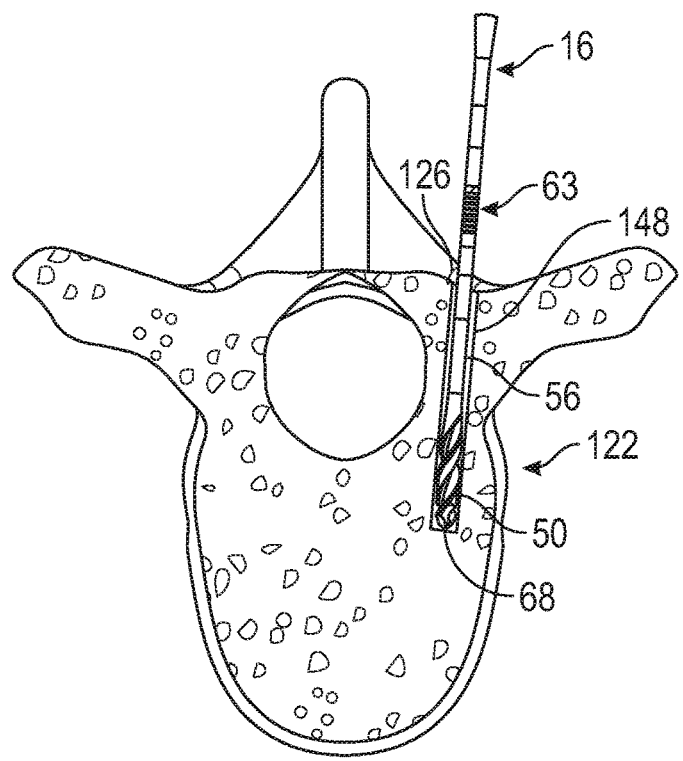
FIG. 11 is a diagrammatic view of the vertebra of FIG. 10 showing the flexible drill bit of FIGS. 2-5 inserted into the pedicle to form a pilot hole.

FIG. 11 is a diagrammatic view of a cross-section of vertebra 122 of FIG. 10 showing flexible drill bit 16 of FIGS. 2-5 inserted into pedicle 126 to form pilot hole 148. Tip 68 can be positioned in the centering hole formed with probe 124 in FIG. 10, though a centering hole need not be used. Power can be applied to drill bit 16 using powered driver 12 of FIG. 1. In order to find the natural path of cancellous bone 140 within pedicle 126 along cancellous bone canal 126A, drill bit 16 can be rotated at very slow speeds, about one to three rotations or revolutions per second, and minimal force can be applied by the surgeon on powered driver 12 to hold drill bit 16 against vertebra 122. As such, cutting head 50 of drill bit can remove bone from the centering hole and will remove cancellous bone 140 after any cortical bone 138 at outer cortical wall 126B is removed. Drill bit 16 will continue to remove cancellous bone 140 as powered driver 12 is pushed into pedicel 126. If drill bit 16 becomes misaligned from axis $A_P$, cutting head may engage cortical bone 138 within pedicle 126 at interior cortical wall 126C or interior cortical wall 126D. Flexible drill bit 16 can transmit the force of the impact of cutting head 50 on cortical bone 138 through second drive shaft 56 all the way through drill bit 16 to powered driver 12, where the surgeon can receive a tactile input of the impact. For example, the surgeon can feel a vibration through handle 20 (FIG. 1). As such, the surgeon can reposition powered driver 12 to realign drill bit 16 along axis $A_P$. The diameter of second drive shaft 56 relative to the size of cutting head 50 and first drive shaft 52 permits the force of the impact of cutting head 50 on cortical bone 138 to be transmitted to first drive shaft 52 via vibration. Additionally, the size and shape of drive shaft 56 permits drive shaft 56 to flex and bend in reaction to impacting cortical bone 138 such that cutting head 50 deflects away from cortical bone 138. After maintaining or correcting the orientation of drill bit 16 along axis $A_P$, drill bit 16 can be pushed into vertebra along axis $A_P$ until the desired depth is reached. Indicators 63 can be used to determine that the desired depth has been reached. In various examples, drill bit 16 can be penetrated into pedicle 126 to a depth in the range of approximately 1.5 cm to approximately 5.0 cm. After drill bit 16 is removed, a ball tip probe (not shown) or a sounding probe such as the one shown in FIG. 14, can be inserted into pilot hole 148 to confirm the integrity of pedicel 126. For example, the ball tip probe can be moved around within pilot hole 148 so that a surgeon can manually fell if pedicle 126 has been or not been breached and that the depth is appropriate, such as for the desired pedicel screw, e.g., pedicel screw 80.

Figure 15:
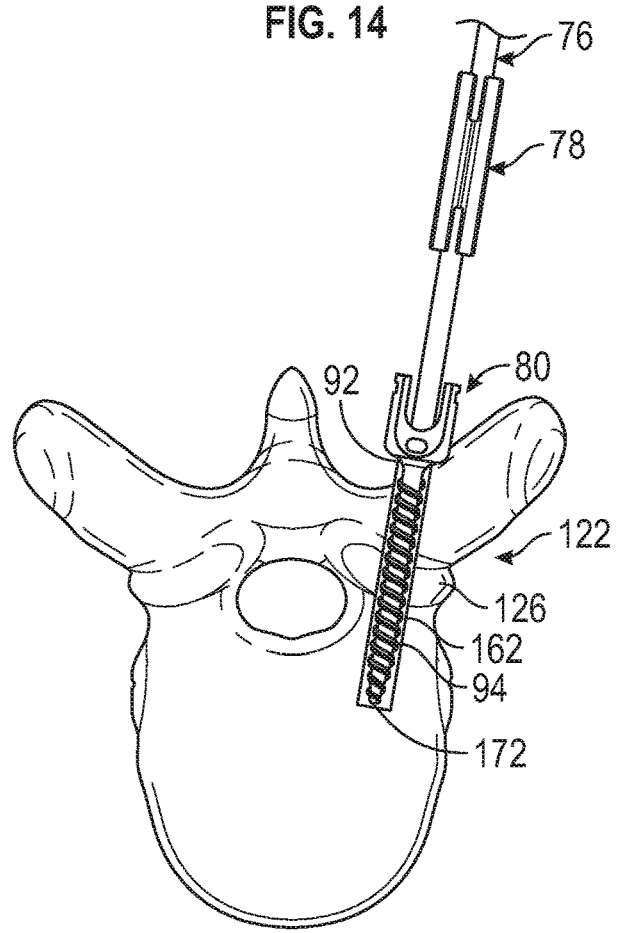
FIG. 15 is a diagrammatic view of the vertebra of FIG. 14 showing a pedicle screw being inserted into the pedicle screw hole using a powered driver shaft with a sliding sleeve device.

In an example, cutting head 50 of drill bit 16 can be smaller than the diameter of threaded shaft 94 of pedicle screw 80, as is shown in FIGS. 11 and 15. In an example, bone canals produced by cutting head 50 can be in the range of approximately 1.5 mm to 2. 5 mm for such configurations. In such cases, the bone canal formed by drill bit 16 can be widened via another enlarging drill bit having a cutting head with a diameter approximating that of threaded shaft 94 of pedicle screw or a blunt ended reamer having a cutting diameter approximating that of threaded shaft 94, such as reamer probe 150 of FIG. 12. Drill bits used for enlarging or widening of a bone canal already formed can additionally include flexible fastener shafts described herein, e.g. having one or both of a tapered shaft and a bulbous cutting head. In examples, flexible drill bits used in combination with these enlarging drill bits and blunt ended reamers can have diameters in the range of about 2.0 mm to 3.0 mm. In other examples, cutting head 50 of drill bit 16 can be sized to have a diameter approximating that of threaded shaft 94 of pedicle screw 80 to be attached to the vertebra, such as approximately 2.0 mm up to the largest diameter fastener used in spinal procedures, e.g. 3.0 mm, and can have one or both of a tapered shaft and a bulbous cutting head.

Figure 12:
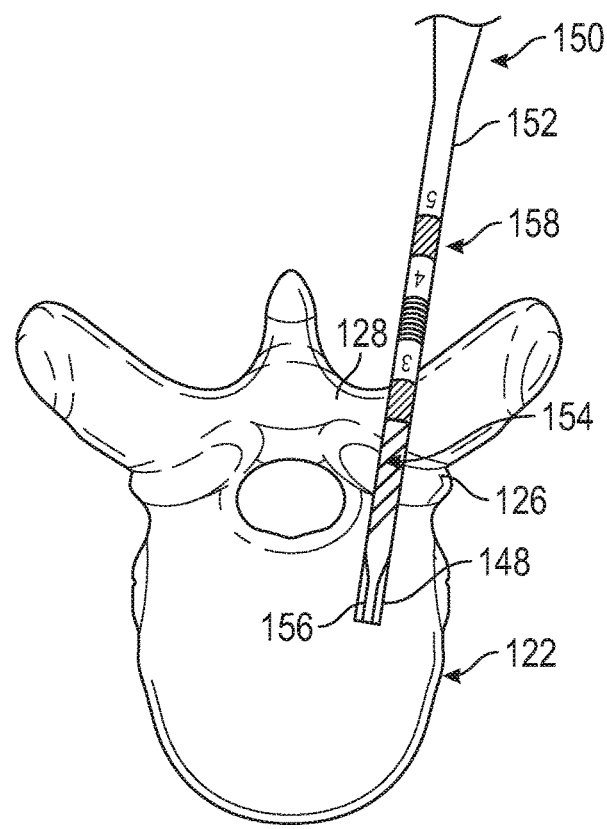
FIG. 12 is a diagrammatic view of the vertebra of FIG. 11 showing a reamer probe inserted into the pilot hole of FIG. 11 to widen the pilot hole.

FIG. 12 is a diagrammatic view of a cross-section of vertebra 122 of FIG. 11 showing reamer probe 150 inserted into pilot hole 148 of FIG. 11 to widen pilot hole 148. Reamer probe 150 can comprise drive shaft 152, drill portion 154, blunt tip 156 and indicators 158. Reamer probe 150 can be used to widen a portion of the length of pilot hole 148 extending into cortical bone 138.

Reamer probe 150 can be used to expand, or further dilate, pilot hole 148 and produce a straight trajectory along axis $A_P$. Reamer probe 150 can comprise drive shaft 152 that can couple to a gear system, such as gear systems 14 or 74, and drill portion 154 that can cut into pilot hole 148. Drill portion 154 has a wider diameter than cutting head 50. In an example, drill portion 154 has a diameter that corresponds to the minor diameter of threaded shaft 94 (i.e., the diameter of shaft 94 not including the thread) of pedicle screw 80. Reamer probe 150 can also comprise blunt tip 156 that can be configured to not cut bone. Reamer probe 150 can be advanced with approximately the same force that flexible drill bit 16 is advanced and at approximately the same rotational speed to avoid damaging or penetrating cortical bone 138. Reamer probe 150 can self-center within pilot hole 148. Blunt tip 156 can have a length that can span the region of cancellous bone 140 within body 136 of vertebra 122 for pilot hole 148. In other words, when reamer probe 150 is fully inserted into pilot hole 148, blunt tip 156 will engage the end of pilot hole 148 and extend across cancellous bone 140 while drill portion 154 spans across cortical bone 138 to widen pilot hole 148 to a new, larger diameter. In an example, drill portion 154 can be configured to extend over the first 20 mm of the length of threaded shaft 94 (measured from head 92) of pedicle screw 80 (FIG. 6) because cancellous bone 140 of vertebra 122 does not need to be widened to receive threaded shaft 94. Indicators 158, which can be configured the same as indicators 63, can be used to determine or verify the depth of widened pilot hole 148. In various examples, reamer probe 150 can be penetrated into pedicle 126 to a depth in the range of approximately 1.5 cm to approximately 5.0 cm. Sliding sleeve 78 can additionally be configured for use with reamer probe 150.

Figure 13:
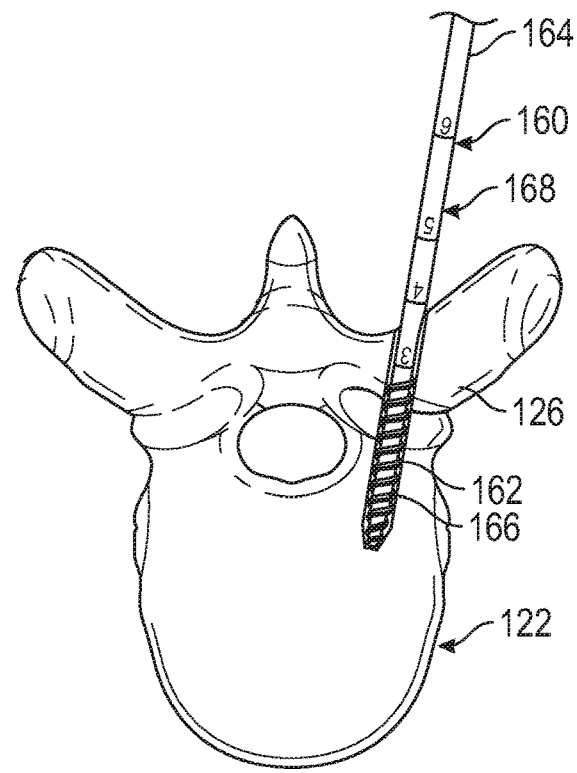
FIG. 13 is a diagrammatic view of the vertebra of FIG. 12 showing a tap inserted into the widened pilot hole to form threading on a pedicle screw hole.

FIG. 13 is a diagrammatic view of a cross-section of vertebra 122 of FIG. 12 showing tap 160 inserted into widened pilot hole 148 to form threading on pedicle screw hole 162. Tap 160 can comprise drive shaft 164, tap portion 166 and indicators 168. Drive shaft 164 can be coupled to powered driver as described herein to rotate tap portion 166. Tap portion 166 can include cutting edges to cut thread channels into pedicle screw hole 162, particularly along cortical bone 138. The thread channels can be configured to mate with thread on threaded shaft 94 of pedicle screw 80 (FIG. 6). In various examples, tap 160 can be penetrated into pedicle 126 to a depth in the range of approximately 1.5 cm to approximately 5.0 cm. Tap 160 can be removed from pedicle screw hole 162 by rotating drive shaft 164 is reverse using powered driver 12. As such, pedicle screw hole 162 is in a prepared condition for receiving pedicle screw 80. However, not all of the steps described with reference to FIGS. 12 and 13 need be performed to couple pedicle screw 80 to vertebra 122. For example, threaded shaft 94 can be directly threaded into pilot hole 148. Sliding sleeve 78 can additionally be configured for use with tap 160.

Figure 14:
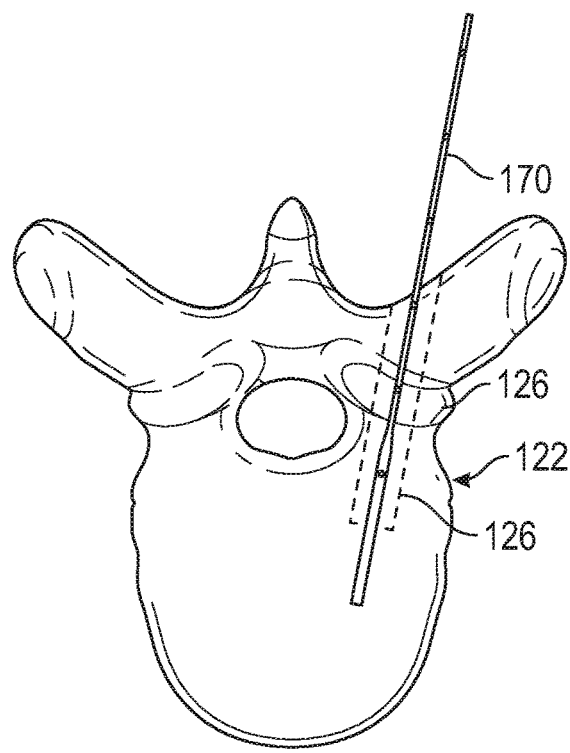
FIG. 14 is a diagrammatic view of the vertebra of FIG. 13 showing a sounding probe inserted into the pedicle screw hole of FIG. 13 to confirm pedicle integrity of the pedicle screw hole.

FIG. 14 is a diagrammatic view of a cross-section of vertebra 122 of FIG. 13 showing sounding probe 170 inserted into pedicle screw hole 162 of FIG. 13 to confirm pedicle integrity of pedicle screw hole 162. Sounding probe 170 may be used at any point after drilling using flexible drill bit 16 in the pedicle preparation process to confirm pedicle integrity, trajectory, and/or threads tapped into vertebra 122. Sounding probe 170 can comprise a small-diameter blunt instrument that can be manually moved around within pilot hole 148 or pedicle screw hole 162 to probe cortical bone 138 to verify that cortical bone 138 is intact. After a surgeon determines that pedicle screw hole 162 is intact or otherwise finally prepared, pedicle screw 80 can be inserted therein.

FIG. 15 is a diagrammatic view of a cross-section of vertebra 122 of FIG. 14 showing pedicle screw 80 being inserted into pedicle screw hole 162 using powered driver shaft 76 with sleeve 78. Tip 90 of driver shaft 76 can be inserted into a socket within head 92. A surgeon can grasp sliding sleeve 78 to steady driver shaft 76 and guide tip 172 of fastener shaft 94 into engagement with the opening of pedicle screw hole 162. As discussed above, driver shaft 76 can be coupled to powered driver 12 to cause rotation of pedicle screw 80 through driver shaft 76. Rotation of threaded shaft 94 can cause thread on threaded shaft 94 to engage pedicle screw hole 162, whether tapped with tap 160 (FIG. 13) or not. Threaded shaft 94 can be rotated until head 92 engages pedicle 126. The surgeon can move sliding sleeve 78 along driver shaft 76 as threaded shaft 94 progresses into pedicle screw hole 162.

Figure 16:
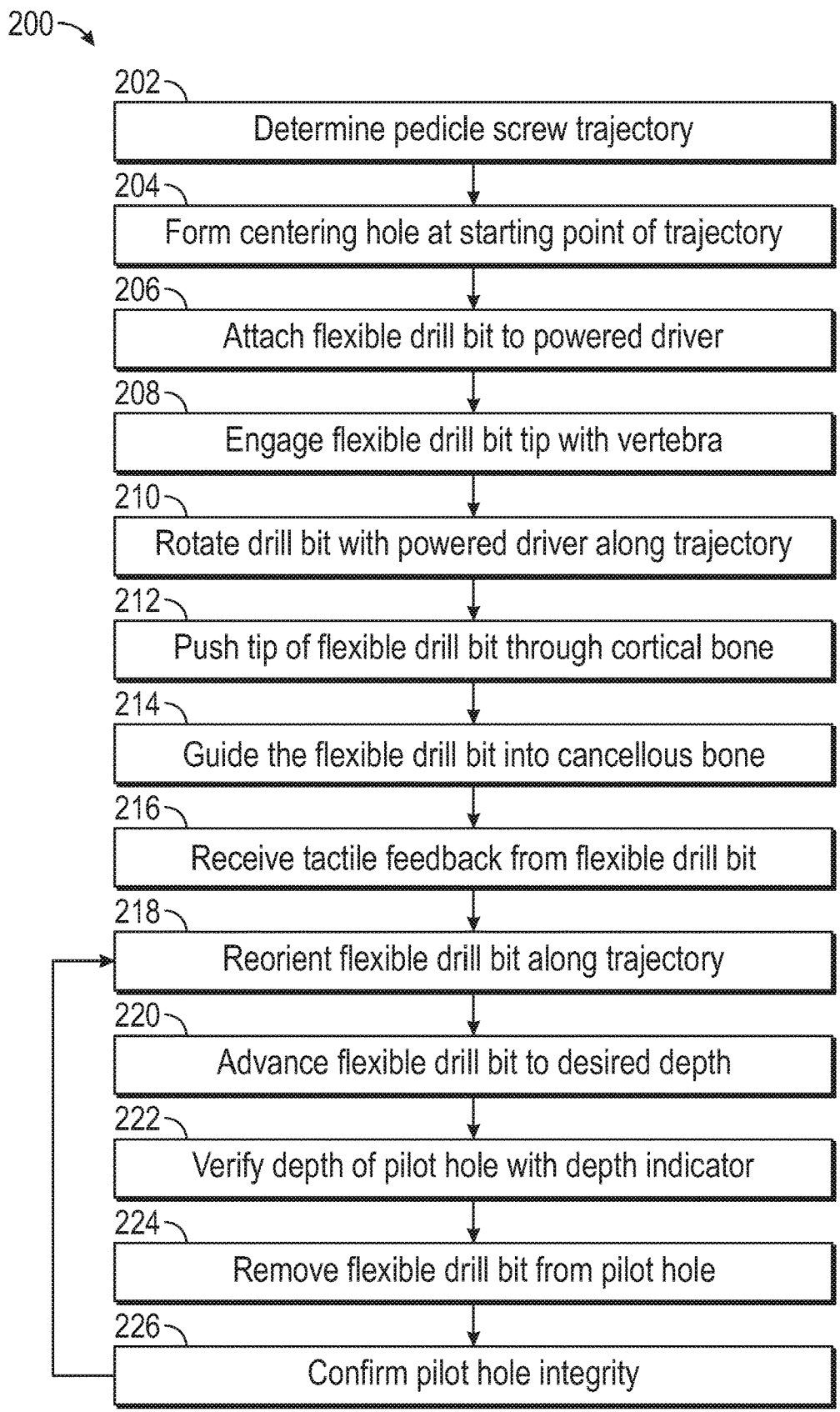
FIG. 16 is a line diagram illustrating steps of a method for forming a pilot hole using a flexible drill bit and a powered driver in accordance with the systems and methods described herein.

FIG. 16 is a line diagram illustrating steps of method 200 for forming a pilot hole using a flexible drill bit and a powered driver in accordance with the systems and methods described herein. The following steps are discussed in an exemplary order, but the discussed steps may be performed in a different order and some of the steps may be considered optional.

At step 202, a trajectory for a pedicle screw shaft into a cancellous bone canal of a vertebral pedicle behind a cortical bone wall can be determined. For example, a surgeon can review images, such as x-ray imaging, of a patient to show cancellous bone of the vertebra within cortical bone. A surgeon may also inspect the vertebra intraoperatively to evaluate boney structures, such as a pedicle, a spinous process and a transverse process, to determine an orientation or angle of the cancellous bone canal between the spinous process and the transverse process.

At step 204, a centering hole can be formed in the cortical bone wall. For example, a probe or awl can be used to make a dimple or depression in the cortical bone wall. The centering hole can be made sufficiently deep to receive a tip of a drill bit to prevent the drill bit from slipping off of the bone when rotated. The centering hole can penetrate completely through the cortical bone wall.

At step 206, a shaft of a flexible drill bit can be attached to a powered driver. Engagement features of the flexible drill bit shaft can be locked into the powered driver to receive torque from the powered driver and prevent the flexible drill bit from separating from the powered driver. The flexible drill bit can also include a neck portion with a tapered profile that reduces the diameter of the shaft. The neck portion can connect to a flexible shaft portion that connects to a bulbous cutting head for cutting bone. In other embodiments, the cutting head is not bulbous and has a diameter approximately equal to a diameter of the flexible shaft. The diameter of the cutting head can vary as described herein, depending on if the flexible drill bit shaft is being used to produce only an initial guiding hole or a final canal for the pedicle screw.

At step 208, a tip of a flexible drill bit at the bulbous cutting head can be engaged with the cortical bone wall. The tip can be positioned in a centering hole, but need not be. A shaft of the drill bit can be oriented along a central axis of the determined cancellous bone canal trajectory.

At step 210, the powered driver can be activated to rotate the flexible drill bit. For example, a button of the powered driver can be depressed or partially depressed to activate an electric motor powered by a battery in the powered driver. Alternatively, the powered driver can be powered by an external electricity source. Depression of the button can cause rotation of the flexible drill bit shaft. The flexible drill bit can be rotated by the powered driver at a slow speed. In an example the slow speed can comprise one to three revolutions per second.

At step 212, the tip of the flexible drill bit can be pushed into exterior cortical bone of the vertebra. The flexible drill bit can be maintained in an orientation along the determined cancellous bone canal trajectory. The flexible drill bit can be pushed until the exterior cortical bone wall is penetrated.

At step 214, the flexible drill bit can be guided into cancellous bone within the pedicle of the vertebra. The flexible drill bit can be maintained in the orientation along the determined cancellous bone canal trajectory. However, it may be possible for the flexible drill bit to become misaligned or for the determined cancellous bone canal trajectory to be not adequately aligned with the anatomical cancellous bone canal in the pedicle.

At step 216, a surgeon can receive tactile feedback generated with the flexible drill bit. The operator can monitor the flexible drill bit to receive the tactile feedback. The tactile feedback can comprise a received vibration from the flexible drill bit, a perceived change in orientation of the flexible drill bit, a perceived change in the rotational speed of the flexible drill bit, or a perceived change in the rate at which the flexible drill bit is advanced into the bone. The tactile feedback can be generated by engagement of the cutting head of the flexible drill bit with cortical bone inside of the pedicle. The flexible drill bit can flex or bend to prevent or inhibit the cutting head from penetrating straight into the cortical bone, thereby eliminating or minimizing cutting of the cortical bone and penetration of the vertebral foramen.

At step 218, the orientation of the flexible drill bit can be adjusted to disengage the cutting head from the cortical bone. In an example, the flexible drill bit can be reoriented so as to align with the central axis of the determined cancellous bone canal trajectory. However, as indicated, the determined cancellous bone canal trajectory may not represent the actual cancellous bone canal path. As such, the flexible drill bit can be reoriented to move the cutting head away from the sensed interior cortical bone from the tactile feedback. That is, if the surgeon senses that the tactile feedback indicates the cutting head has moved medially to engage cortical bone alongside the vertebral foramen, the surgeon can move the cutting head laterally away from the vertebral foramen even if that moves the flexible drill bit off of the determined trajectory.

At step 220, the flexible drill bit can be advanced along the path determined in step 218 to the desired depth. That is, after corrective action in reaction to the generated tactile feedback, the flexible drill bit can be pushed further into the cancellous bone to form a pedicle screw hole to receive a threaded fastener of a pedicle screw. The depth of the pedicle screw hole can vary as described herein, depending on if the flexible drill bit shaft is being used to produce only an initial guiding hole or a final canal for the pedicle screw. In examples, the pedicle screw hole depth can correspond to a length of the threaded fastener of the pedicle screw.

At step 220, the depth of the pedicle screw hole can be verified with indicators located on the flexible drill bit. The outer surface of the pedicle at the outer cortical wall can be aligned with graduation marks or graduation bands on the flexible drill bit. The surgeon can monitor progress of the flexible drill bit against these indicators as the flexible drill bit is advanced.

At step 222, the flexible drill bit can be removed from the pedicle screw hole. Application of rotational power to the flexible drill bit from the powered driver can be stopped and the flexible drill bit can be withdrawn from the vertebra. In an example, the powered driver can apply reverse rotational power to the flexible drill bit to facilitate removal.

At step 224, the pedicle screw hole can be checked with a probe to verify the integrity of the bone. For example, the probe can be manually manipulated within the pedicle screw hole to look for anomalies in the bone, weak spots in the bone or holes penetrating into the vertebral foramen. If no issues are detected with the probe, the pedicle screw hole can be finished as desired by the surgeon and the pedicle screw can be attached to the pedicel screw hole, such as by using the systems and methods described herein. If any issues are detected, the surgeon can take corrective action to restore the integrity of the cortical bone along the vertebral foramen, can choose to not implant he pedicle screw, or can decide that further drilling with the flexible drill bit is required to straighten or deepen the pedicle screw hole. As discussed herein, the diameter of the pedicle screw hole can be widened with a widening or enlarging drill bit having a larger cutting head, a reamer or an awl if a flexible drill bit having a diameter corresponding to a diameter of the pedicle screw is not used.

The systems and methods discussed in the present application can be useful in implanting bone fasteners or pedicle screws into boney structures of vertebra. In particular, the systems and methods allow for the safe use of powered drill bits by preserving the ability of a surgeon to use instinct and tactile feedback to feel changes in resistance to movement of the drill bit at a powered driver. The systems and methods include use of a flexible drill bit that is shaped and configured to transmit forces, such as vibrations, on a cutting head of the drill bit back to the surgeon through the drill bit shaft and the powered driver. As such, the systems and methods can be effective in reducing the risk of penetrating a vertebral foramen of the vertebra with a drill bit. As such, the systems and methods are effective in reducing potential injury to the spine and spinal cord.

VARIOUS NOTES & EXAMPLES

Example 1 can include or use subject matter such as a method of implanting a bone anchor in a vertebra that can comprise engaging a tip of a flexible drill bit with boney structure of the vertebra, rotating the flexible drill bit at a slow speed, pushing the drill bit into exterior cortical bone of the boney structure of the vertebra, guiding the flexible drill bit into cancellous bone of the vertebra, receiving a tactile output generated by the flexible drill bit indicating resistance of interior cortical bone of the boney structure through the flexible drill bit, and reorienting a trajectory of the flexible drill bit toward the cancellous bone of the vertebra in reaction to the tactile output.

Example 2 can include, or can optionally be combined with the subject matter of Example 1, to optionally include rotating the flexible drill bit at a slow speed with a powered driver.

Example 3 can include, or can optionally be combined with the subject matter of one or any combination of Examples 1 or 2 to optionally include rotating the flexible drill bit at approximately one to three revolutions per second.

Example 4 can include, or can optionally be combined with the subject matter of one or any combination of Examples 1 through 3 to optionally include receiving tactile output at the powered driver by feeling vibration of the flexible drill bit.

Example 5 can include, or can optionally be combined with the subject matter of one or any combination of Examples 1 through 4 to optionally include feeling vibration of the flexible drill bit by feeling bending of the flexible drill bit.

Example 6 can include, or can optionally be combined with the subject matter of one or any combination of Examples 1 through 5 to optionally include bending of the flexible drill bit by bending the flexible drill bit between a necked-down shaft portion and a bulbous drill tip.

Example 7 can include, or can optionally be combined with the subject matter of one or any combination of Examples 1 through 6 to optionally include engaging the tip of the flexible drill bit with the boney structure of the vertebra by forming a centering hole in the exterior cortical bone of the boney structure, and engaging the tip of the flexible drill bit with the centering hole.

Example 8 can include, or can optionally be combined with the subject matter of one or any combination of Examples 1 through 7 to optionally include withdrawing the flexible drill bit from the boney structure to leave a bone canal, and confirming formation of the bone canal with a ball tip probe.

Example 9 can include, or can optionally be combined with the subject matter of one or any combination of Examples 1 through 8 to optionally include withdrawing the flexible drill bit from the boney structure to leave a bone canal, widening the bone canal with an enlarging drill bit to a diameter of a threaded fastener of the bone anchor, and inserting the threaded fastener into the widened bone canal.

Example 10 withdrawing the flexible drill bit from the boney structure to leave a bone canal, widening the bone canal with a reamer to a diameter of a threaded fastener of the bone anchor, inserting the threaded fastener into the widened bone canal.

Example 11 can include, or can optionally be combined with the subject matter of one or any combination of Examples 1 through 9 to optionally include withdrawing the flexible drill bit from the boney structure to leave a bone canal, and inserting the bone anchor into the bone canal, wherein a flexible drill bit has a diameter corresponding to the threaded shaft of the bone anchor.

Example 12 can include, or can optionally be combined with the subject matter of claim 11 to optionally include checking a depth of the flexible drill bit in the vertebra by referencing cortical bone against indicia provided on a flexible portion of the flexible drill bit.

Example 13 can include, or can optionally be combined with the subject matter of one or any combination of Examples 1 through 12 to optionally include inserting the bone anchor into the bone canal by coupling a sleeve to a driver shaft, coupling the driver shaft to the bone anchor, grasping the sleeve, guiding the driver shaft toward the boney structure to insert the bone anchor into the bone canal, rotating the driver shaft within the sleeve using a powered driver and translating the sleeve along the driver shaft to guide the bone anchor to the bone canal and to receive the tactile output of the flexible drill bit.

Example 14 can include or use subject matter such as a method of implanting a pedicle screw into a pedicle of a vertebra that can comprise determining a trajectory for a pedicle screw shaft into a cancellous bone canal behind a cortical bone wall to avoid interior cortical bone, engaging a tip of a drill bit having a tapered shaft with a starting point of the trajectory on the cortical bone wall of the pedicle of the vertebra, rotating the drill bit using rotational input from a powered driver, pushing the powered driver to penetrate the tip of the drill bit through the cortical bone wall along the trajectory, guiding the drill bit into the cancellous bone canal, sensing engagement of the tip of the drill bit with the interior cortical bone, and reorienting the drill bit along the trajectory away from the interior cortical bone.

Example 15 can include, or can optionally be combined with the subject matter of Example 14, to optionally include producing a centering hole in the cortical bone wall at the starting point before engaging the tip of the drill bit with the cortical bone wall.

Example 16 can include, or can optionally be combined with the subject matter of one or any combination of Examples 14 or 15 to optionally include sensing engagement of the tip of the drill bit by receiving a tactile feedback at the powered driver.

Example 17 can include, or can optionally be combined with the subject matter of one or any combination of Examples 14 through 16 to optionally include tactile feedback that can comprise a vibration of the drill bit transmitted to the powered driver.

Example 18 can include, or can optionally be combined with the subject matter of one or any combination of Examples 14 through 17 to optionally include a drill bit comprising a first shaft portion for coupling to a driver, a tapered portion extending from the first shaft portion at a first end to a reduced diameter at a second end, and a second shaft portion extending from the second end of the tapered portion, the second shaft portion having a diameter of in the range of 1.0 mm to 2.0 mm, wherein the vibration of the drill bit is caused by bending of the second shaft portion of the drill bit, and vibration of the drill bit can be caused by bending of a necked-down shaft of the drill bit.

Example 19 can include, or can optionally be combined with the subject matter of one or any combination of Examples 14 through 18 to optionally include bending of the necked-down shaft of the drill bit that can cause the tip of the drill bit to deflect away from the interior cortical bone.

Example 20 can include, or can optionally be combined with the subject matter of one or any combination of Examples 13 through 19 to optionally include withdrawing the flexible drill bit from the vertebra to leave a bone canal, confirming formation of the bone canal with a ball tip probe, and inserting a bone anchor into the bone canal.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of implanting a bone anchor in a vertebra, the method comprising:
engaging a tip of a flexible drill bit with boney structure of the vertebra;
rotating the flexible drill bit at a slow speed;
pushing the drill bit into exterior cortical bone of the boney structure of the vertebra;
guiding the flexible drill bit into cancellous bone of the vertebra;
receiving a tactile output generated by the flexible drill bit indicating resistance of interior cortical bone of the boney structure through the flexible drill bit; and
reorienting a trajectory of the flexible drill bit toward the cancellous bone of the vertebra in reaction to the tactile output;
wherein feeling vibration of the flexible drill bit comprises feeling bending of the flexible drill bit.

2. The method of claim 1, wherein rotating the flexible drill bit at a slow speed comprises rotating the flexible drill bit with a powered driver.

3. The method of claim 2, wherein rotating the flexible drill bit at a slow speed comprises rotating the flexible drill bit at approximately one to three revolutions per second.

4. The method of claim 2, further comprising receiving the tactile output at the powered driver by feeling vibration of the flexible drill bit.

5. The method of claim 1, wherein bending of the flexible drill bit comprises bending the flexible drill bit between a necked-down shaft portion and a bulbous drill tip.

6. The method of claim 1, wherein engaging the tip of the flexible drill bit with the boney structure of the vertebra further comprises:
forming a centering hole in the exterior cortical bone of the boney structure; and
engaging the tip of the flexible drill bit with the centering hole.

7. The method of claim 1, further comprising:
withdrawing the flexible drill bit from the boney structure to leave a bone canal; and
confirming formation of the bone canal with a ball tip probe.

8. The method of claim 1, further comprising:
withdrawing the flexible drill bit from the boney structure to leave a bone canal;
widening the bone canal with an enlarging drill bit to a diameter of a threaded fastener of the bone anchor; and
inserting the threaded fastener into the widened bone canal.

9. The method of claim 1, further comprising:
withdrawing the flexible drill bit from the boney structure to leave a bone canal;
widening the bone canal with a reamer to a diameter of a threaded fastener of the bone anchor; and
inserting the threaded fastener into the widened bone canal.

10. The method of claim 1, further comprising:
withdrawing the flexible drill bit from the boney structure to leave a bone canal; and
inserting a bone anchor into the bone canal, wherein the flexible drill bit has a diameter equal to or smaller than a threaded shaft of the bone anchor.

11. The method of claim 1, further comprising checking a depth of the flexible drill bit in the vertebra by referencing cortical bone against indicia provided on a flexible portion of the flexible drill bit.

12. The method of claim 9, wherein inserting the bone anchor into the bone canal comprises:
coupling a sleeve to a driver shaft;
coupling the driver shaft to the bone anchor;
grasping the sleeve;
guiding the driver shaft toward the boney structure to insert the bone anchor into the bone canal;
rotating the driver shaft within the sleeve using a powered driver; and
translating the sleeve along the driver shaft to guide the bone anchor to the bone canal and to receive the tactile output of the flexible drill bit.

13. A method of implanting a pedicle screw into a pedicle of a vertebra, the method comprising:
determining a trajectory for a pedicle screw shaft into a cancellous bone canal behind a cortical bone wall to avoid interior cortical bone;
engaging a tip of a drill bit having a tapered shaft with a starting point of the trajectory on the cortical bone wall of the pedicle of the vertebra;
rotating the drill bit using rotational input from a powered driver;
pushing the powered driver to penetrate the tip of the drill bit through the cortical bone wall along the trajectory;
guiding the drill bit into the cancellous bone canal;
sensing engagement of the tip of the drill bit with the interior cortical bone; and
reorienting the drill bit along the trajectory away from the interior cortical bone,
wherein sensing engagement of the tip of the drill bit comprises receiving a tactile feedback at the powered driver;
wherein the tactile feedback comprises a vibration of the drill bit transmitted to the powered driver; and
wherein the drill bit comprises:
a first shaft portion for coupling to a driver;
a tapered portion extending from the first shaft portion at a first end to a reduced diameter at a second end; and
a second shaft portion extending from the second end of the tapered portion, the second shaft portion having a diameter of in the range of 1.0 mm to 2.0 mm;
wherein the vibration of the drill bit is caused by bending of the second shaft portion of the drill bit.

14. The method of claim 13, further comprising producing a centering hole in the cortical bone wall at the starting point before engaging the tip of the drill bit with the cortical bone wall.

15. The method of claim 13, wherein bending of the necked-down shaft of the drill bit causes the tip of the drill bit to deflect away from the interior cortical bone.

16. The method of claim 13, further comprising:
withdrawing the flexible drill bit from the vertebra to leave a bone canal;
confirming formation of the bone canal with a ball tip probe; and
inserting a bone anchor into the bone canal.

17. The method of claim 1, wherein the bending occurs proximal of the distal bulbous drill tip.

18. A method of implanting a bone anchor in a vertebra, the method comprising:
engaging a tip of a flexible drill bit with boney structure of the vertebra;
rotating the flexible drill bit at a slow speed;
pushing the drill bit into exterior cortical bone of the boney structure of the vertebra;
guiding the flexible drill bit into cancellous bone of the vertebra;
receiving a tactile output generated by the flexible drill bit indicating resistance of interior cortical bone of the boney structure through the flexible drill bit; and
reorienting a trajectory of the flexible drill bit toward the cancellous bone of the vertebra in reaction to the tactile output;
wherein inserting the bone anchor into the bone canal comprises:
coupling a sleeve to a driver shaft;
coupling the driver shaft to the bone anchor;
grasping the sleeve;
guiding the driver shaft toward the boney structure to insert the bone anchor into the bone canal;
rotating the driver shaft within the sleeve using a powered driver; and
translating the sleeve along the driver shaft to guide the bone anchor to the bone canal and to receive the tactile output of the flexible drill bit.

* * * * *